US008852093B2

(12) United States Patent
Clapp et al.

(10) Patent No.: US 8,852,093 B2
(45) Date of Patent: Oct. 7, 2014

(54) HOME CARE LOGISTICS AND QUALITY ASSURANCE SYSTEM

(75) Inventors: Geoffrey Clapp, Sunnyvale, CA (US); Stephen J. Brown, Woodside, CA (US)

(73) Assignee: Health Hero Network, Inc., Redwood City, CA (US)

( * ) Notice: Subject to any disclaimer, the term of this patent is extended or adjusted under 35 U.S.C. 154(b) by 827 days.

(21) Appl. No.: 11/686,020

(22) Filed: Mar. 14, 2007

(65) Prior Publication Data

US 2008/0058615 A1      Mar. 6, 2008

Related U.S. Application Data

(63) Continuation-in-part of application No. 11/643,491, filed on Dec. 21, 2006, now Pat. No. 7,789,828.

(60) Provisional application No. 60/841,368, filed on Aug. 31, 2006.

(51) Int. Cl.
| | | |
|---|---|---|
| *A61B 5/00* | (2006.01) | |
| *G06Q 10/00* | (2012.01) | |
| *G06Q 50/00* | (2012.01) | |
| *G06Q 10/06* | (2012.01) | |
| *G06F 19/00* | (2011.01) | |
| *A61B 5/145* | (2006.01) | |
| *A61B 5/0205* | (2006.01) | |

(52) U.S. Cl.
CPC .............. *G06F 19/327* (2013.01); *G06Q 10/06* (2013.01); *G06F 19/3418* (2013.01); *A61B 5/14532* (2013.01); *A61B 5/02055* (2013.01)
USPC .................... 600/300; 705/2; 705/3; 600/301

(58) Field of Classification Search
CPC ....... G06Q 10/00; G06Q 10/06; G06Q 50/22; A61B 5/0002; A61B 5/0015–5/0024; A61B 5/1112–5/1114; A61B 5/02; A61B 5/0205; A61B 5/021; G06F 19/322–19/328; G06F 19/3418; G06F 19/3425; G06F 19/3431; G06F 19/3437; G06F 19/3487
USPC ........................................................ 705/2–5
See application file for complete search history.

(56) References Cited

U.S. PATENT DOCUMENTS

| | | | |
|---|---|---|---|
| 5,553,609 A * | 9/1996 | Chen et al. ..................... 600/301 |
| 6,847,892 B2 | 1/2005 | Zhou et al. | |
| 7,099,835 B2 * | 8/2006 | Williams, III ............... 705/27.1 |
| 7,154,397 B2 * | 12/2006 | Zerhusen et al. .......... 340/573.1 |
| 7,249,036 B2 * | 7/2007 | Bayne .............................. 705/2 |

(Continued)

FOREIGN PATENT DOCUMENTS

EP              1622057           2/2006

*Primary Examiner* — William Thomson
*Assistant Examiner* — Sirley Jian
(74) *Attorney, Agent, or Firm* — Suiter Swantz pc llo

(57) ABSTRACT

A mobile home care logistics and quality assurance system to enhance the efficiency, accuracy, accountability, and overall level of care for nurses visiting patients in their home. The system has a patient home health communication interface to establish a communication between a patient and a central server to receive instructions from and to transmit collected data/information to a remote server. The remote server generates various reports including a home visit prioritization report and a routing report based on the collected and stored data. The information and reports are used for billing, performance reviews, and patient data for assessment of each home-care nurse's in-field assignments.

20 Claims, 8 Drawing Sheets

(56) References Cited

U.S. PATENT DOCUMENTS

| | | |
|---|---|---|
| 7,570,152 B2 * | 8/2009 | Smith et al. .............. 340/286.07 |
| 7,789,828 B2 * | 9/2010 | Clapp ........................... 600/301 |
| 8,019,622 B2 * | 9/2011 | Kaboff et al. ..................... 705/2 |
| 8,682,686 B2 * | 3/2014 | Warner et al. ..................... 705/2 |
| 2001/0014863 A1 * | 8/2001 | Williams, III .................... 705/1 |
| 2001/0044732 A1 * | 11/2001 | Maus et al. ....................... 705/3 |
| 2002/0019584 A1 * | 2/2002 | Schulze et al. ................ 600/300 |
| 2002/0077841 A1 * | 6/2002 | Thompson ........................ 705/1 |
| 2003/0069752 A1 * | 4/2003 | LeDain et al. .................... 705/2 |
| 2005/0021369 A1 | 1/2005 | Cohen et al. |
| 2005/0060198 A1 * | 3/2005 | Bayne ............................... 705/2 |
| 2005/0108050 A1 | 5/2005 | Knapheide |
| 2005/0131740 A1 * | 6/2005 | Massenzio et al. ............... 705/2 |
| 2006/0030890 A1 * | 2/2006 | Cosentino et al. ................ 607/5 |
| 2006/0036471 A1 * | 2/2006 | Sanjay-Gopal et al. .......... 705/3 |
| 2006/0064030 A1 * | 3/2006 | Cosentino et al. ............ 128/920 |
| 2007/0040692 A1 * | 2/2007 | Smith et al. ................. 340/573.1 |
| 2009/0132276 A1 * | 5/2009 | Petera ............................... 705/2 |
| 2009/0182575 A1 * | 7/2009 | Warner et al. ..................... 705/2 |
| 2010/0174551 A1 * | 7/2010 | Kiley ................................ 705/2 |
| 2010/0198608 A1 * | 8/2010 | Kaboff et al. ..................... 705/2 |

* cited by examiner

FIG 4

HOME CARE LOGISTICS AND QUALITY ASSURANCE SYSTEM

CROSS REFERENCE TO RELATED APPLICATIONS

The present application is a continuation-in-part of U.S. patent application Ser. No. 11/643,491 filed Dec. 21, 2006 now U.S. Pat. No. 7,789,828. The present application also claims the benefit under 35 U.S.C. §119 of U.S. Provisional Application No. 60/841,368, filed on Aug. 31, 2006. Said U.S. patent application Ser. No. 11/643,491 and U.S. Provisional Application No. 60/841,368 are hereby incorporated by reference in their entirety.

TECHNICAL FIELD

This invention generally relates to health care management systems and more particularly to a home health care management system and to a home care logistics and quality assurance system to enhance the efficiency, accuracy, accountability, and overall level of care for nurses visiting patients in their home.

BACKGROUND

Until recently, the hospital has always been the center of the healthcare system. The explosion of health care technology, however, has resulted in new concepts like home-based health care services and telemedicine services. If given a choice, people with chronic illness prefer to stay at home and receive appropriate medical care through home-based health care services for economic and personal considerations rather than in a hospital. In the United States, more than 90 million people have chronic illness. The top 5 chronic illnesses are heart diseases, cancer, stroke, chronic obstructive pulmonary disease and diabetes. The home-based heath care services provide personal health care services to individuals or patients who require special attention as a lower cost alternative to extended stays in a hospital or convalescent homes. Indeed, for many patients with a chronic illness who require intermittent skilled nursing care, the therapy is often better provided in a home environment than in a hospital, in accordance with a plan of treatment established by the patient's physician. Generally the home health care visits are made by a registered nurse, certified nursing assistant, physical therapist, occupational therapist, speech or language pathologist, medical social care giver, psychiatric nurse, registered dietician, or a semi-skilled employee based on a preset schedule to carry out an allocated or assigned task in accordance with a treatment plan.

A prime concern of the health care provider is to manage and control the delivery and the quality of the home health care service. When an exceptional circumstance has arisen to put a particular patient at risk, it is often difficult to quickly assess the risk for each patient being cared for and to identify the particular patient requiring special attention. The health care providers have minimal emergency control measures to deal with an exceptionally critical situation adequately. Hence there is a need to collect and control patient data efficiently and effectively to provide adequate medical care during an emergency at the earliest instance. Also, there is a need to monitor home health care services personnel to acquire patient data and to collect data regarding the medical assistance provided to the patient to ensure quality of service, prevent the generation of errors and fraudulent activity in medical insurance claiming process.

The U.S. Patent Publication No. 20050021369 discloses a system and method for managing context relevant information and a display provided with a wireless information device to provide a user with context relevant information based on the identity of the user, location of the device and proximity of the device to persons.

The U.S. Patent Publication No. 20050131740 discloses a management tool for health care providers. The system has a communication system to couple a server computer to a field information device so that health care giver may access patient data information stored on a server and the server may receive an indication of the location of a visiting nurse.

The EP Patent No. 1622057 discloses a method and a system for providing a home health care and information and communication technology platform. The system has a communication interface to provide a communication between mobile terminals and a central server to permit the exchange of data to ensure that the data is synchronized with mobile terminals and central server.

The WO Patent No. 2005038691 discloses a health care delivery information management system, has an interface processor to receive an identification data of a patient. The display processor generates a data representing a specific type of heath information for a given patient in response to a user selected item.

Thus the currently available health care service monitoring systems and health care service providing systems do not have adequate systems and solutions to monitor and track the visit of health care personal to patient home on a priority basis and to improve the reliability and consistency of the health care services. Hence there is a need to monitor the visit of a visiting nurse remotely in a non-obtrusive manner, to collect the activities of the visiting nurse and patient to generate a prioritized report to enhance the efficiency, accuracy, accountability, and overall level of care for visiting nurses.

OBJECT OF THIS INVENTION

The primary object of this invention is to provide a system to track and control visiting nurses at patient homes to collect nurse visit data, data regarding the activities of the nurse at a patient's home, to collect data regarding the treatment provided to patient, the patient medical history data to enhance the efficiency, accuracy, accountability and overall level of care for visiting nurses.

Another object of this invention is to provide a system to collect home monitoring data to generate and provide a prioritized visit report for patients and a routing report to a nursing agency and to a visiting nurse.

Another object of this invention is to provide a system to provide a desired training and educational information with respect to a special need or medical treatment or medical condition of a patient to a visiting nurse on demand or request.

Another object of this invention is to provide a system to track the visit and services offered by the visiting nurse to a patient at home.

Another object of this invention is to provide a system to generate and send a report regarding the visit of a nurse to a central office or to a nursing agency.

Another object of this invention is to provide a system to provide an adequate home monitoring service.

Another object of this invention is to provide a system to improve the data forwarding method used for sending a data from a central office or a nursing agency to a visiting nurse efficiently.

Another object of this invention is to provide a system to improve the efficiency of a data collection process and a home care system.

Another object of this invention is to provide a system to correlate the home monitoring data and prioritized home care activity with actual activity of home care personnel to measure and evaluate the quality of service offered by a visiting nurse to ensure suitable billing process.

Another object of this invention is to provide a system to prevent generation of a fraudulent data, misinformation and errors in billing and patient care data.

SUMMARY OF THE INVENTION

The above-mentioned shortcomings, disadvantages and the problems addressed herein, are understood by reading and studying the following specification. The embodiment herein provides a home care logistics and quality assurance system to monitor and track the visiting of a nurse at a patient home to collect nurse visit data and patient data to provide required assistance in terms of training and educational data to a visiting nurse to improve the efficiency, accuracy, accountability and overall efficiency of the system.

According to one embodiment of this invention, the system has a patient home health communication interface to establish a communication between a patient and a central server to receive instructions from and to transmit collected data to a remote server. The patient interface has a microprocessor and a memory to store a scripted content, the program instructions, and collected data. The remote server has databases for storing scripted content, collected patient data, and applications for communicating with the patient interface system. The remote server generates various reports including a home visit prioritization report and a routing report based on the collected and stored data. The data/information are combined with a map data to create an optimized and prioritized route for a visiting home care nurse. A homecare provider interface provided with a computer is connected to a remote server to view patient data and reports, to enter patient data, to assign programs to patients, and to send messages to patients. The generated prioritized patient visit report and a routing report are provided to a visiting nurse calling on the patient at home through a mobile communication device.

BRIEF DESCRIPTION OF DRAWINGS

FIG. 4 shows a front view of a graphical user interface for prioritized call/visit list for visiting nurse on a nursing agency computer connected to home care logistics and quality assurance system according to one embodiment of this invention.

DETAILED DESCRIPTION OF THE PREFERRED EMBODIMENT

Figure 1:
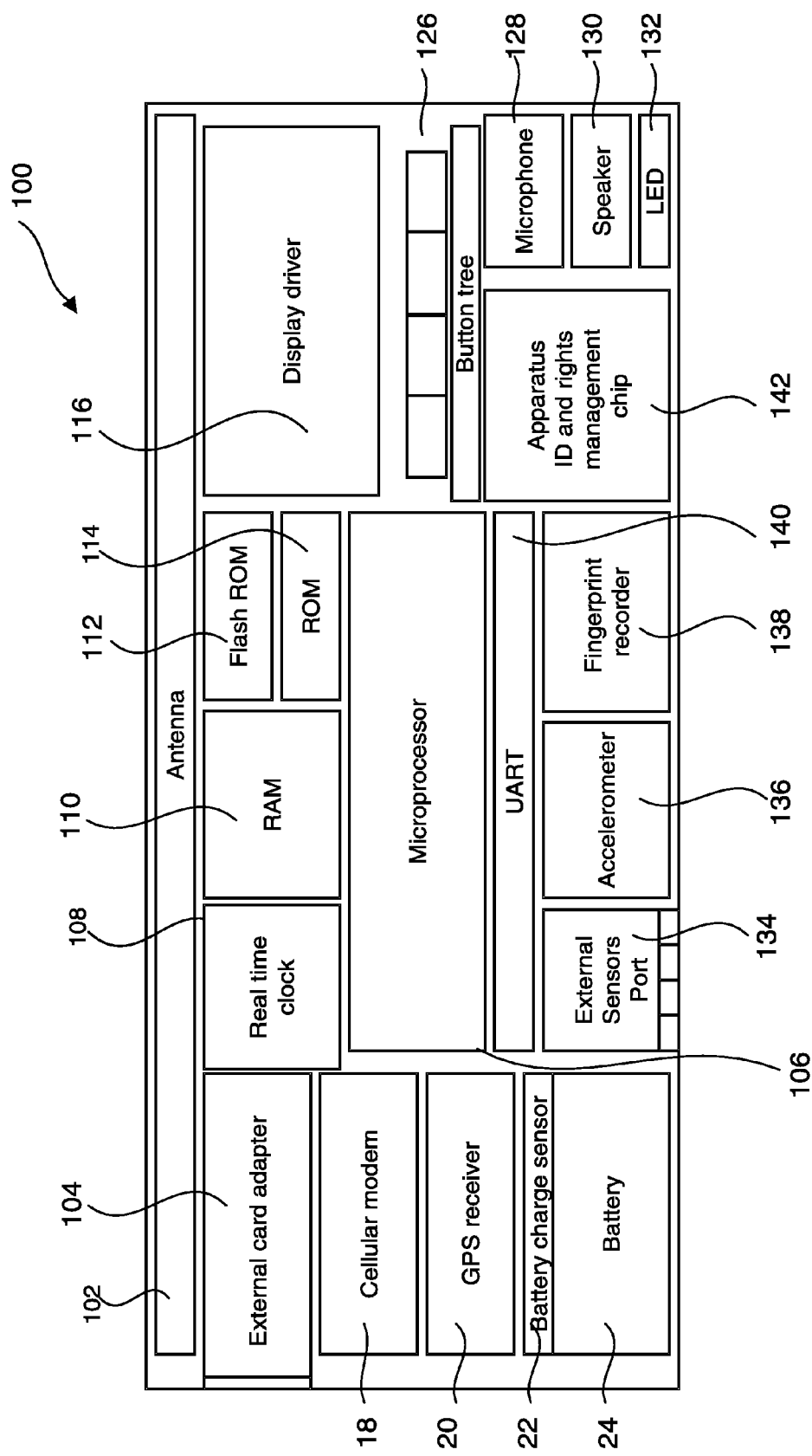
FIG. 1 shows a block diagram of the components present in a home care logistics and quality assurance system, according to one embodiment of this invention.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

A preferred embodiment provides a home care logistics and quality assurance system. The system has a patient home health communication interface for communication between a patient and a central server to collect patient data and data related to the visit of a visiting nurse to a patient at home. The patient home health communication interface has a microprocessor and a memory for storing a scripted content, the program instructions, and the collected data. The patient home health communication interface is connected through a communication channel to a remote server to receive the instructions from the remote server and to transmit the collected data to the remote server. The remote server has databases for storing the scripted content, the collected patient data, and the applications for communicating with the patient interface system. The remote server processes the received data from the patient interface for generating various reports including a home visit prioritization report and routing report. The data/information is combined with map data to create an optimized and prioritized route for a visiting home care nurse. The optimized and prioritized route for a nurse is forwarded to a nursing agency and to an individual visiting nurse through a personal communication device like mobile phone, personal digital assistant, etc.

A mobile telephone unit has a location awareness technology such as a GPS unit so that the mobile unit records the nurse GPS location in the memory of the mobile unit at regular time intervals. The nurse GPS unit records the route information including the time spent with each patient location. The mobile unit transmits the information to the remote server. The information sent is used by the remote server for generating various reports. The information is used for billing, performance reviews, and patient data for assessment of each homecare nurse's in-field assignments. The mobile unit enables a visiting nurse to receive patient scripts and educational content pertaining to patient health and the data that results from patient interaction with the scripted content. A homecare provider interface is provided with a computer that is connected to a remote server to view the patient data and reports, to enter patient data, to assign programs to patients, and to send messages to the patients.

FIG. 1 shows a block diagram of components in a patient home communication interface 100 in a home care logistics and quality assurance system. The patient home communication interface 100 has an external sensor port for coupling with sensors like, blood pressure sensor, blood glucose level monitor, pulse and heart rate variability measuring unit, pulseoximeter device, blood coagulation monitor, respiratory sensor, weight scale and body fat sensor and other sensors like smoke detector, humidity sensor, fire alarm, gas leak sensor, etc. The output data from the sensors are analyzed with a microprocessor 106 and stored in the memory units like RAM 110, ROM 114 and Flash ROM 112. The patient interface has a GPS receiver 20 to obtain location data from a Global Positioning System. The identification data of the patient device is stored with an apparatus ID and rights management chip 142. The identification data of the patient device, the positional data of the patient device and the sensor output data is transmitted along with a time data acquired from a real time clock 108 to a central server through wireless communication device or transceiver, such as a universal asynchronous receiver and transmitter (UART) 140. The patient device also interacts with a mobile communication device owned by a visiting nurse through a cellular modem 18 in a non-obtrusive manner to collect the arrival time of a nurse and the out going time of the nurse. The received data from a central server and the stored data are displayed on a monitor by a display driver 116. All the functional components of the system are supplied with an electric power from a battery 24. The residual battery level is monitored with a battery charge sensor 22 and the output of the battery sensor 22 is indicated through a LED 132. Any abnormal condition of the device and alert message are communicated through a speaker 130, and a microphone 128. A button tree 126 containing several buttons is provided to enable a user to input a data or to activate a specific device component. The device has an external card adapter 104 to receive a data card to receive and transmit a data with an external device. An antenna 102 is provided to transmit or receive a data from an external device through a wireless communication system. A universal asynchronous receiver and transmitter (UART) 140 is provided to provide a serial data communication between the system and the peripheral units. A finger print recorder 138 is provided to read and register the fingerprint of the user to authenticate a user. An accelerometer 136 is provided to estimate the location of the patient interface device when the system could not receive location data from a Global Positioning System.

Figure 2:
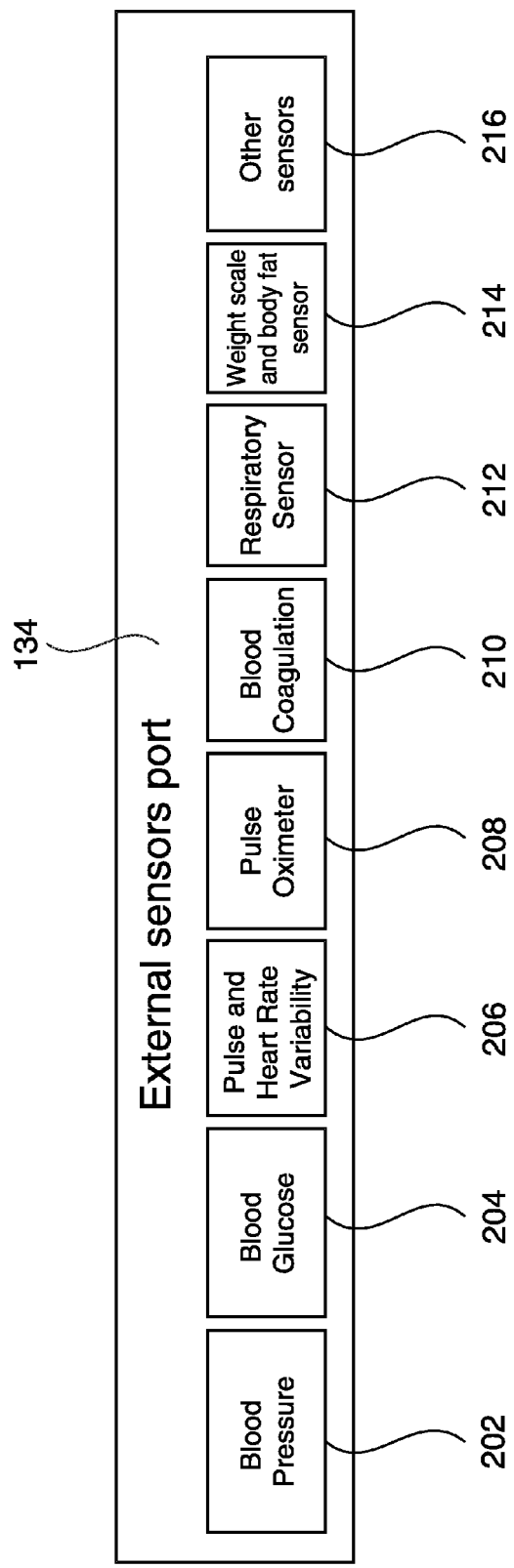
FIG. 2 shows a block diagram of an external sensor port connected with various sensors in a home care logistics and quality assurance system according to one embodiment of this invention.

FIG. 2 shows a block diagram of various sensors connected to an external sensor port 134 provided in a patient home communication interface device. The plurality of sensors consist of blood pressure monitor 202, blood glucose level monitor 204, Pulse and heart rate variability monitor 206, Pulse oximeter device 208, blood coagulation monitor 210, respiratory sensor 212, weight scale and body fat sensor 214 and other sensors 216 like smoke detector, fire alarm detector, gas leak sensor, humidity sensor etc provided to measure blood pressure level, blood glucose level, pulse and heart rate, blood coagulation condition, respiratory condition, body weight and body fat content of a patient and smoke, fire, gas leak, and humidity level of an environment in which a patient resides.

Figure 3:
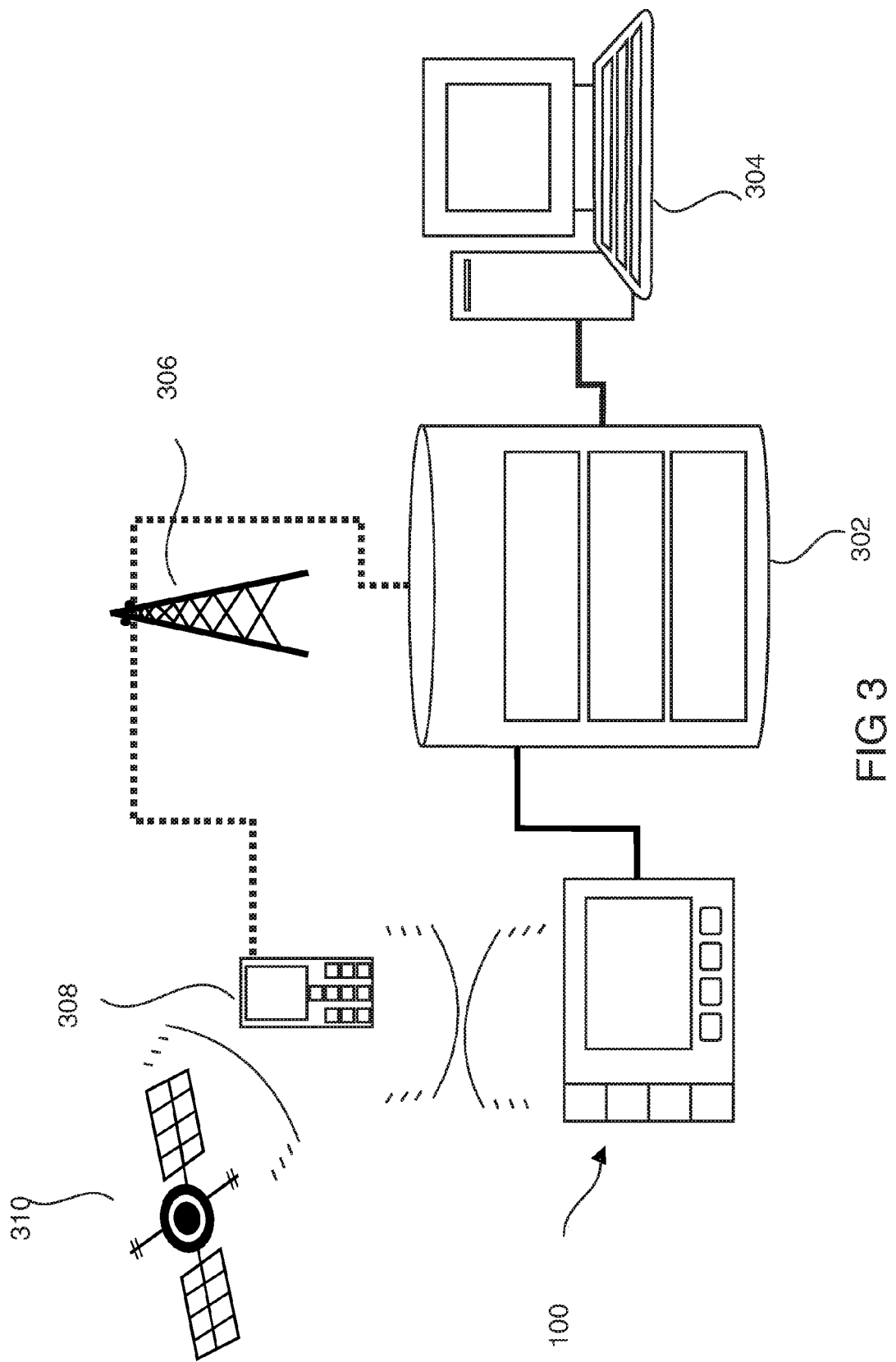
FIG. 3 shows a functional block diagram of a home care logistics and quality assurance system according to one embodiment of this invention.

FIG. 3 shows a block diagram of a home monitoring system and home care logistics system in which a patient home interface communication device 100 is connected to a remote server 302 through a communication channel to transmit and receive patient data, location data, nurse visit data and treatment data to the remote server 302. The remote server 302 has databases for scripted content, collected patient data and vital signs data, software for analysis and report generation and visiting nurse call/visit data. The remote server 302 processes the received data to generate a prioritized patient report and a routing report. The routing report is generated by indicating the priority and the location of patients along with travel route on a map. The remote server 302 is connected to a home care agency 304, or a nursing agency through a communication channel to transmit the generated prioritized patient report and the routing report to the home care agency 304 or the nursing agency. A mobile communication device 308 like a mobile telephone, personal digital assistant, etc., is connected to the remote server 302 through a mobile communication system 306 to receive the generated prioritized patient report and routing report from the remote server. The mobile communication device has a GPS receiver unit to receive the location data of the device from a Global Positioning System GPS or GPS satellite 310 at periodic intervals. The received location data are stored in the memory of the mobile communication device 308. The mobile communication device is connected through a wireless communication system to the patient home interface unit 100 to receive the sensed patient data periodically at regular intervals so that the location of the mobile communication unit and the patient data are sent to the remote server periodically to enable the server to generate a visiting nurse visit data to a patient home, whenever the visiting nurse calls on each patient based on the received prioritized report. The received nurse visit data is compared with the sent prioritized patient data and the routing data to estimate the efficiency of the home care system. The visiting nurse is also enabled to receive updated medical assistance procedures with respect to a patient and the training with respect to a critical condition of the patient from a remote server 302 on demand and based on the received sensor data from the patient interface unit.

Figure 4:
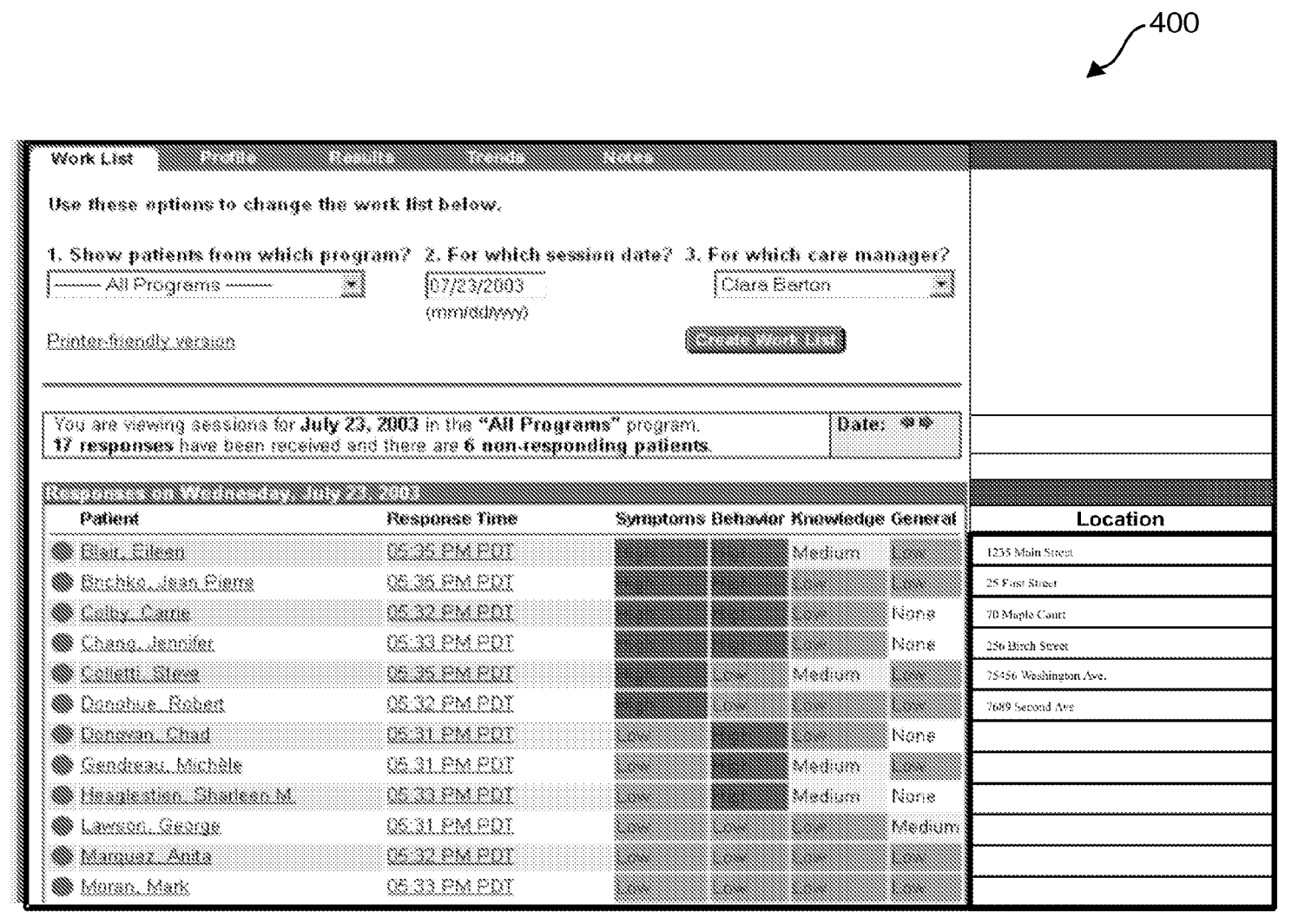

FIG. 4 shows an exemplary view of the graphical user interface 400 displayed on a mobile unit of a visiting nurse who calls on a patient at home. The graphical user interface displays a prioritized report of a patient in which a patient name, response time, priority assigned to a patient based on received patient data at a given time and the location of a patient data. The prioritized patient report enables a visiting nurse to call and attend patients based on the priority of each patient.

Figure 5:
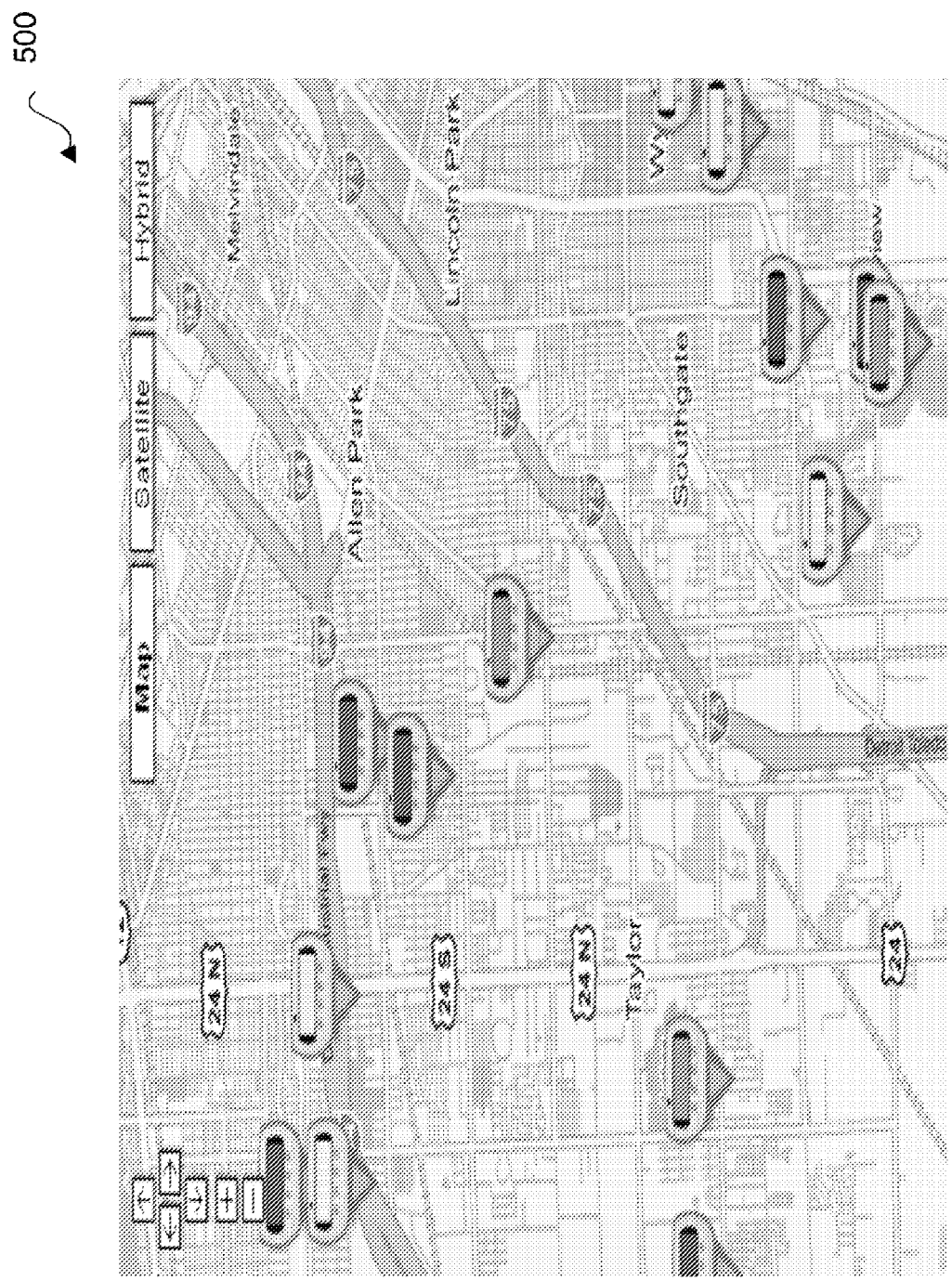
FIG. 5 shows an example of a map data interface displayed on a mobile communication device connected to a home care logistics and control system according to one embodiment of this invention.

FIG. 5 shows an example of map data 500 sent to a visiting nurse from a remote server through a mobile communication device or on the nurse station 304. The map indicates a route for visiting patients based on the assigned priority to each patient based on the received patient data. The map also displays the location of each patient home along with the assigned priority of each patient. The routing data along with prioritized patient data enables a visiting nurse to call on the patients efficiently and effectively to provide medical assistance to the patients based on the estimated priority. The map can be zoomed to any level. The patients can be plotted on the map based on search parameters. The movement of visiting nurses can be charted over time. The alerts can be flagged with a visible indicator or flashing icon. The compliance of a visiting nurse with an issued prioritized list may be monitored. The map may be reprioritized before and after a nurse visit, based on the incoming patient data of the patients who have not been visited.

Figure 6:
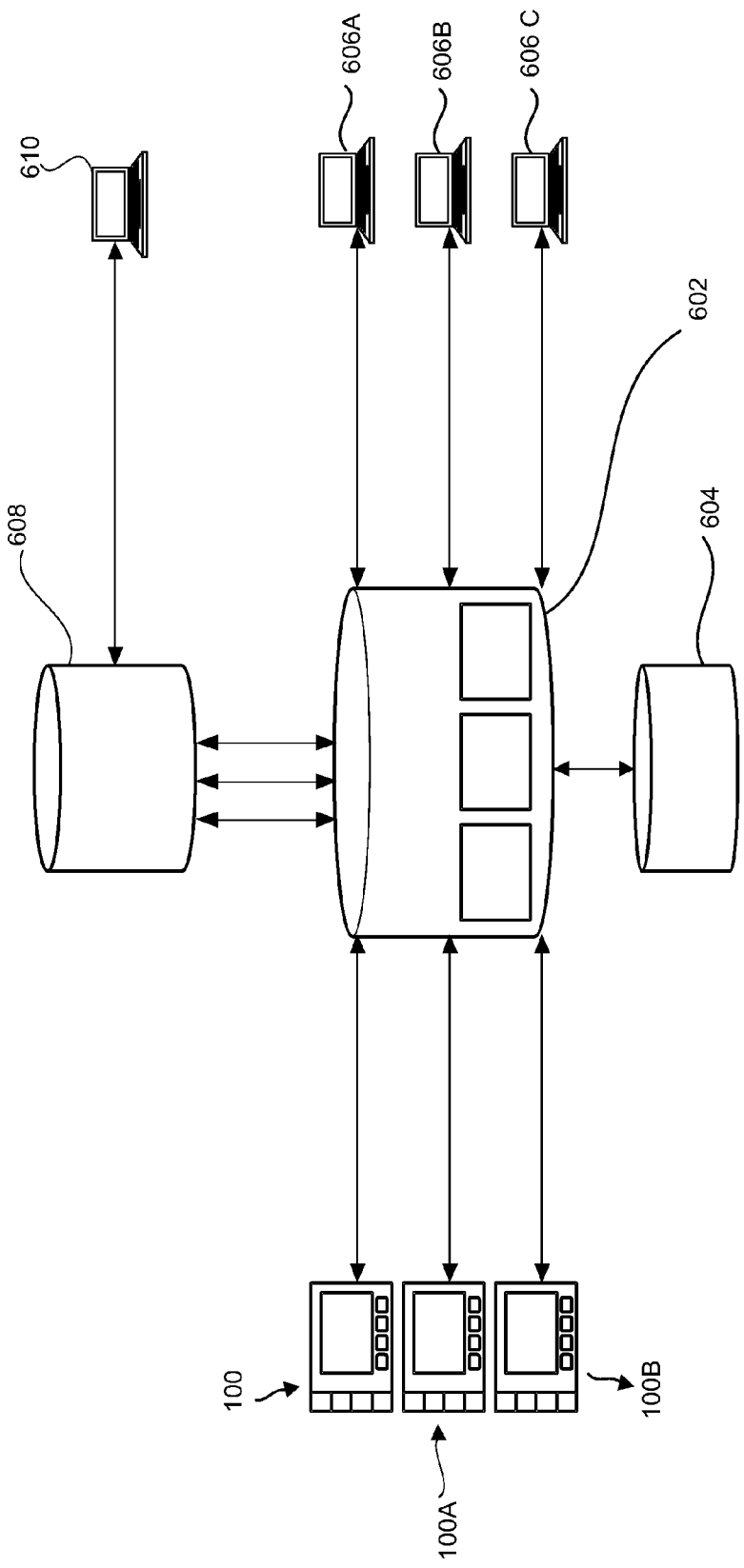
FIG. 6 shows a block diagram of a monitoring agency connected to a home care logistics and quality assurance system according to one embodiment of this invention.

FIG. 6 shows the block diagram of the quality evaluation system provided with a quality manager to monitor and estimate the efficiency of the nurse call visit and the efficiency of the home care logistic systems. The patient home interface devices 100, 100A, 100B are connected through a communication channel to a database for patient data and applications 602 provided in a remote server to transfer the collected patient data from several sensors and the nurse visit data. A quality manager 610 is connected to the remote server through a quality service monitoring device 608 so that the quality manager 610 receives nurse visit data of a patient home and compares the same with the generated prioritized patient visit data to evaluate the efficiency of the nurse call visit and the efficiency of the logistics system. A mapping application database 604 is connected to the database for application and for patient and agency data. The mapping application stores the map data containing a prioritized patient data and routing data 602 generated based on the received patient data. A home care agency 606A, 606B, 606C, is connected to the database for application and for patient and agency data 602 to access the patient data, the nurse visit data, the generated prioritized patient data, route data and map data so that the generated prioritized patient data, route data and map data is forwarded to a mobile communication device held by a visiting nurse.

Figure 7:
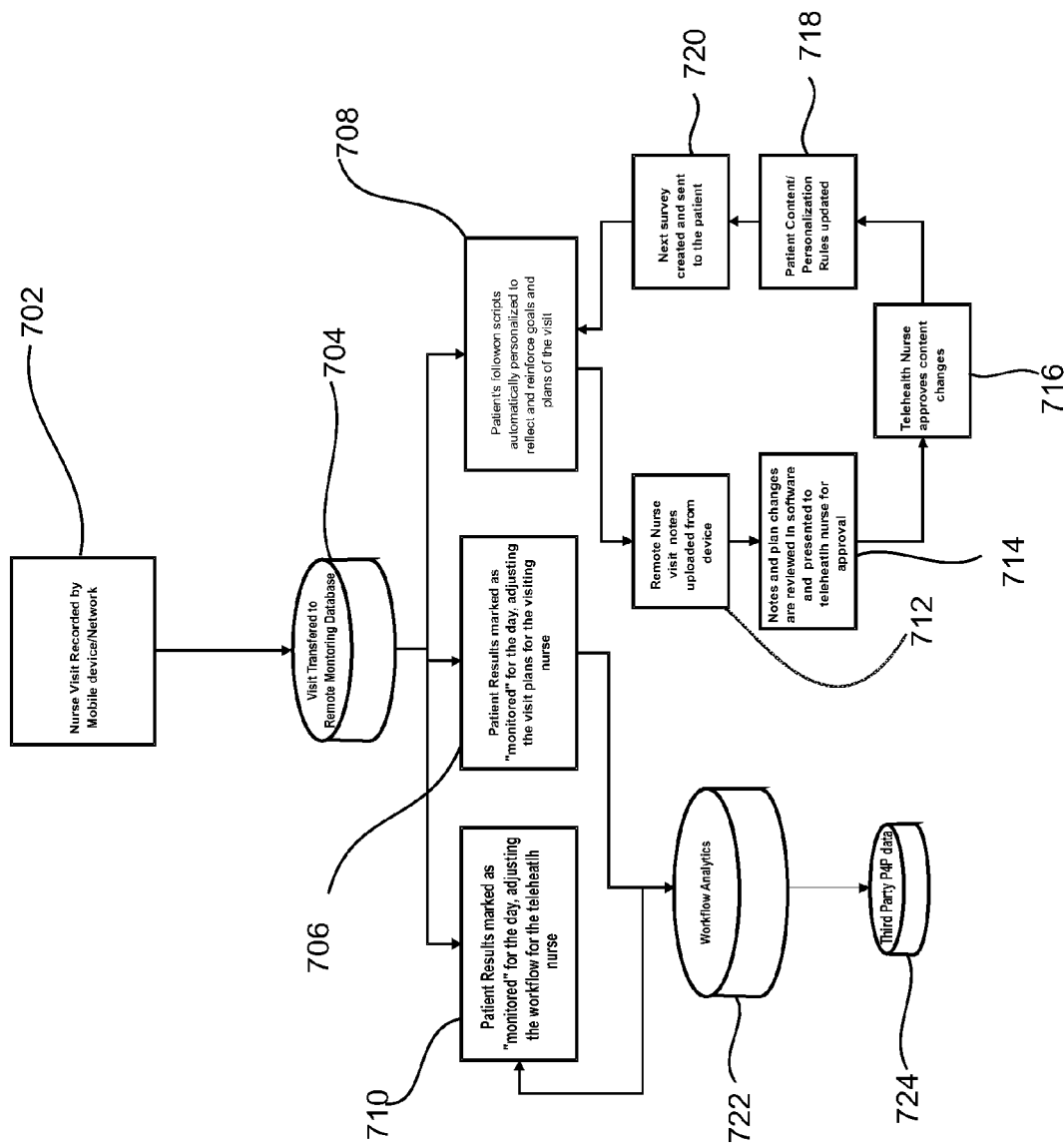
FIG. 7 shows a flowchart explaining the operation of one embodiment of a home care logistics and quality assurance system using risk feedback.

FIG. 7 shows a flowchart indicating the operation of a home care logistics and quality assurance system using a risk feedback. The visit of a nurse to a patient's home is recorded by a mobile communication device like a mobile telephone or personal digital assistant held by a visiting nurse in the step 702. Whenever a nurse visits a patient's home, the location of the patient's home is received from a GPS system and stored in the memory of the mobile communication device. The stored location data and the patient data collected from the sensors attached to the patient interface unit are transmitted to a remote server or a central server for storage at a remote monitoring database in the step 704. The personalized individual patient profile stored in the database at the remote server is updated and the nurse visit is marked based on the received patient data from the nurse through the mobile phone in the step 706. The visiting program of a visiting nurse for the patients is also adjusted for the day based on the received patient data. The adjusted visiting plans of a nurse for a day is forwarded to a work flow analysis module for adjusting the work flow of a telehealth nurse. The patient's follow-on program mentioned in the personalized patient profiles is automatically prioritized to reflect and reinforce the goals and the plans of a visit by a remote server in the step 708 based on the collected patient data from the home interface and the received patient data from the nurse after a visit. The work flow of a telehealth nurse is also adjusted and the visit of the nurse program for a patient is marked on the individual patient profile in the step 710 based on the received patient data from the nurse and the out put of the work flow analysis module. The received patient data are transferred to work flow analytics module for processing in the step 722. The processed data from the workflow analytics module are transferred to a third party P4P database in the step 724. A remote nurse visiting a patient at home uploads the visit notes to a nursing agency in the step 712. The received notes and the visit plan changes are reviewed using a software in the step 714. The received data from the visiting nurse and the modified visit plan changes are provided to a telehealth nurse for approval. The telehealth nurse approves the content changes through the step 716. The patient data and the personalization rules are updated based on the approved content in the step 718. A next survey is created and sent to a patient based on the updated patient content and personalization rules in the step 720. The generated survey data is transmitted to a remote server.

Figure 8:
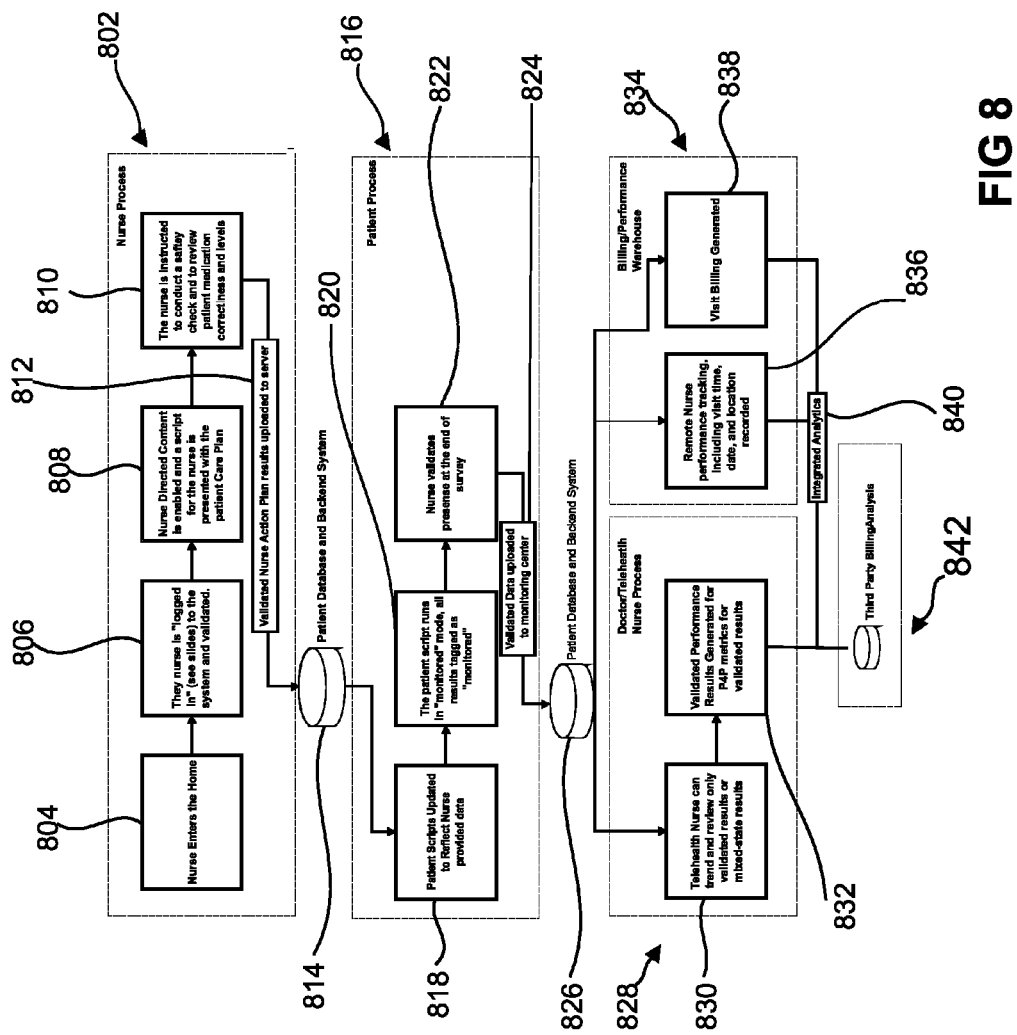
FIG. 8 shows a flowchart of one embodiment of a home care logistics and quality assurance system using validated patient results.

FIG. 8 shows a flowchart explaining the operation of one embodiment of a home care logistics and quality assurance system using the validated patient results. The entire operations are classified into several groups of operations, namely the nurse process 802, the patient process 816, doctor/telehealth nurse process 828, the billing and performance process 834 and third party billing analysis process 842. A nurse enters the home of a patient in the step 804. The nurse is logged in to the system and validated by the step 806. The nurse is logged in using a local identification process or by a Bluetooth tagging process or by using RFID tag or other RF identification devices or security login panel or swipe card, or biometric data such as retinal or finger print scan. A script for the visiting nurse is generated based on the received data from the visiting nurse and presented to the visiting nurse with a patient care plan in the step 808. The nurse is instructed to conduct a safety check and to review the patient medication correctiveness and levels in the step 810. The validated nurse action plan results are uploaded to server in the step 812. The validated and uploaded nurse action plans are transmitted to a patient data base and back end system in the step 814. The patient scripts are updated to reflect the data provided by the visiting nurse in the step 818. The patient scripts are processed in a monitored mode and all the process results are tagged as monitored in the step 820. The nurse validates the presence at the end of a survey in the step 822. The validated data are uploaded to a monitoring center in the step 824 and to a patient database and backend system by the step 826. In the telehealth nurse process, the telehealth nurse may trend and review the validated results or mixed stat results in the step 830. The validated performance results generated for P4P metrics for validated results in the step 832. The generated and validated performance results are forwarded to a third party billing processor. In the billing process, the performance of a visiting nurse, visiting time, date and location are recorded by the step 836. A billing is generated based on the recorded data in the step 838. The generated billings data are sent to an integrated analytics module in the step 840.

It will be obvious for a person of skilled in the art to practice this invention with various modifications. However, all those modifications will be deemed to be covered within the scope if this invention as covered in the claims mentioned hereunder.

We claim:

1. A mobile home care logistics and quality assurance system, comprising:
  a patient home health communication interface system installed at a patient's home, the patient home health communication interface system collects patient data, time stamps the patient data, and transmits collected patient data to a remote server, the patient home health communication interface system includes a location awareness device;
  the remote server communicatively coupled to patient home health communication interface system, the remote server receives collected patient data and stores collected patient data, scripted contents, patient location data and applications for processing collected patient data and for generating reports containing home prioritization data and routing data for visiting patient homes;
  a mobile unit held by a nurse visiting said patient at a home and communicatively coupled to said remote server, said mobile unit receives report data and transmits patient call visit data, the mobile unit includes a location awareness device;
  a home health care service provider interface communicatively coupled to said remote server, said home health care service provider interface receives collected patient data, generated report data and nurse call visit data to provide logistic support to patient at home and to visiting nurse, wherein said remote server generates various reports including a home visit prioritization report and routing report, the remote server generates a map image including a route and a patient priority for a visiting home care nurse based upon collected patient data, a location of the visiting home care nurse and a location of each patient which is transmitted to said mobile unit, the patient home health communication interface system communicates with said mobile unit and is configured to collect an arrival time of said nurse and a departure time of said nurse of a visit of said nurse; and a quality service monitoring device coupled to said remote server, said quality service monitoring device receives nurse visit data, said quality service monitoring device compares the received nurse visit data with prioritized patient visit data to evaluate efficiency.

2. The system according to claim 1 wherein the said patient home health communication interface comprises a microprocessor, a memory that stores scripted content, program instructions and data, a user interface and a communication unit.

3. The system according to claim 1 wherein the patient home health communication interface connects with a plurality of sensors to collect patient data.

4. The system according to claim 3 wherein said plurality of sensors includes any of a blood pressure monitor, a blood glucose level monitor, a pulse and heart rate variability monitor, a pulse oximeter device, a blood coagulation monitor, a respiratory sensor, a weight scale and body fat sensor, a smoke detector, a fire alarm detector, a gas leak sensor, and a humidity sensor.

5. The system according to claim 1, wherein said patient home health communication interface is connected through a communication channel to receive instructions from the said remote server and to transmit collected data to said remote server.

6. The system according to claim 1, wherein the home health care service provider interface includes a computer that connects to said remote server in order to view patient data and reports, enter patient data, assign programs to patients, and send messages to patients.

7. The system according to claim 1, wherein said mobile unit is a portable proxy for the home health care service provider interface.

8. The system according to claim 1, wherein the mobile unit records nurse location in memory of the mobile unit at regular time intervals.

9. The system according to claim 1, wherein said mobile unit transmits information to the said remote server.

10. The system according to claim 1, wherein said mobile unit receives patient scripts and educational content pertaining to patient health.

11. The system according to claim 10, wherein said educational content pertaining to patient health includes updated medical assistance procedures with respect to a particular patient based upon received patient data.

12. The system according to claim 1,
a work flow analysis module, said work flow analysis module adjusts a work flow of particular nurses based on collected patient data and received patient data.

13. The system according to claim 12, wherein work flow analysis module transfers data processed by the work flow analysis module to a third party pay for performance database.

14. A mobile home care logistics and quality assurance method, comprising:

communicatively connecting a remote server with a patient home health care communication interface system, the patient home health communication interface system located at patient's home and collects patient data, time stamps the patient data and transmits collected patient data to the remote server, the patient home health communication interface system includes a location awareness device, the remote server collecting and storing patient data at databases to generate reports containing a patient prioritization data, location data of patients and a routing data for visiting the patients at home;

the remote server transmitting the generated reports to a nurse through a mobile unit held by a nurse visiting a patient at home and collecting data regarding a nurse visit, said mobile unit includes a location awareness device;

the remote server transmitting collected patient data, generated report data and nurse visit data to a home health care service provider interface, the home health care service provider interface providing a logistics support to a patient and to monitor a nurse visit;

the home health care service provider interface transmitting a map image including a route and a patient priority for a visiting home care nurse based upon collected patient data, a location of the visiting home care nurse and a location of each patient to said mobile unit; and the patient home health care communication interface system collecting an arrival time of said nurse and a departure time of said nurse of said nurse visit by interacting with the mobile unit held by the visiting nurse;

a quality service monitoring device receiving nurse visit data; and the quality service monitoring device comparing the received nurse visit data with prioritized patient visit data to evaluate efficiency.

15. The method according to claim 14 wherein the patient home health communication interface is connected to at least one patient data collection sensor.

16. The method according to claim 15 wherein said at least one patient data collection sensor includes any of a blood pressure monitor, a blood glucose level monitor, a pulse and heart rate variability monitor, a pulse oximeter device, a blood coagulation monitor, a respiratory sensor, a weight scale and body fat sensor, a smoke detector, a fire alarm detector, a gas leak sensor, and a humidity sensor.

17. A method according to claim 14, wherein said patient home health communication interface is connected through a communication channel to receive instructions from the remote server and to transmit collected data to the remote server.

18. The method according to claim 14, wherein said mobile unit is a portable proxy for the home health care service provider interface.

19. The method according to claim 14, wherein the mobile unit records nurse location in memory of the mobile unit at regular time intervals.

20. The method according to claim 14, wherein the mobile unit transmits information to the said remote server.

* * * * *